(12) United States Patent
Oetjen (10) Patent No.: US 10,252,506 B2
(45) Date of Patent: *Apr. 9, 2019

(54) METHOD OF PRODUCING A COMPOSITE MULTI-LAYERED PRINTED ABSORBENT ARTICLE

(71) Applicant: The Procter & Gamble Company, Cincinnati, OH (US)

(72) Inventor: David Christopher Oetjen, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/480,415

(22) Filed: Apr. 6, 2017

(65) Prior Publication Data

US 2017/0210110 A1   Jul. 27, 2017

Related U.S. Application Data

(60) Continuation of application No. 14/189,374, filed on Feb. 25, 2014, now Pat. No. 9,642,752, which is a
(Continued)

(51) Int. Cl.
*B32B 37/00* (2006.01)
*A61F 13/00* (2006.01)
(Continued)

(52) U.S. Cl.
CPC ...... *B32B 37/203* (2013.01); *A61F 13/15699* (2013.01); *A61F 13/15723* (2013.01); *A61F 13/15731* (2013.01); *A61F 13/51394* (2013.01); *A61F 13/51496* (2013.01); *B32B 3/28* (2013.01); *B32B 3/30* (2013.01); *B32B 5/022* (2013.01); *B32B 5/024* (2013.01); *B32B 5/08* (2013.01); *B32B 5/142* (2013.01); *B32B 27/12* (2013.01); *B32B 38/0004* (2013.01); *B32B 38/04* (2013.01); *B32B 38/06* (2013.01);
(Continued)

(58) Field of Classification Search
CPC .......... A61F 13/15699; A61F 13/51394; A61F 13/51496; A61F 2013/15243; Y10T 156/1052; Y10T 156/1074; Y10T 156/1089; B32B 2305/20; B32B 2555/00; B32B 2555/02; B32B 27/12; B32B 38/06; B32B 38/145

See application file for complete search history.

(56) References Cited

U.S. PATENT DOCUMENTS 4,324,246 A   4/1982   Mullane et al.
4,342,314 A   8/1982   Radel et al.
(Continued)

FOREIGN PATENT DOCUMENTS

WO   WO 2007/070132   6/2007
WO   WO2009/137311 A1   12/2009

OTHER PUBLICATIONS

International Search Report, PCT/US/2011/056978, 10 pages.
(Continued)

*Primary Examiner* — Linda L Gray
(74) *Attorney, Agent, or Firm* — George H. Leal (57) ABSTRACT

A method for producing a composite multi-layered absorbent article. At least two of the layers include a colored region.

19 Claims, 8 Drawing Sheets

Related U.S. Application Data division of application No. 12/908,519, filed on Oct. 20, 2010, now Pat. No. 8,691,041, which is a continuation-in-part of application No. 12/578,604, filed on Oct. 14, 2009, now Pat. No. 8,539,511, which is a continuation-in-part of application No. 12/548,603, filed on Aug. 27, 2009, now Pat. No. 8,262,633, which is a continuation-in-part of application No. 12/188,543, filed on Aug. 8, 2008, now Pat. No. 7,967,801, which is a continuation-in-part of application No. 12/188,598, filed on Aug. 8, 2008, now Pat. No. 8,058,501.

(51) Int. Cl.

| | | |
|---|---|---|
| *B32B 37/20* | (2006.01) | |
| *A61F 13/513* | (2006.01) | |
| *A61F 13/514* | (2006.01) | |
| *B32B 27/12* | (2006.01) | |
| *B32B 38/06* | (2006.01) | |
| *B32B 38/00* | (2006.01) | |
| *A61F 13/15* | (2006.01) | |
| *B32B 5/02* | (2006.01) | |
| *B32B 5/08* | (2006.01) | |
| *B32B 5/14* | (2006.01) | |
| *B32B 3/28* | (2006.01) | |
| *B32B 3/30* | (2006.01) | |
| *B32B 38/04* | (2006.01) | |

(52) U.S. Cl.
CPC .. *B32B 38/145* (2013.01); *A61F 2013/15243* (2013.01); *B32B 37/20* (2013.01); *B32B 2038/047* (2013.01); *B32B 2255/10* (2013.01); *B32B 2262/02* (2013.01); *B32B 2262/0207* (2013.01); *B32B 2262/0253* (2013.01); *B32B 2262/0276* (2013.01); *B32B 2262/06* (2013.01); *B32B 2262/062* (2013.01); *B32B 2262/067* (2013.01); *B32B 2262/14* (2013.01); *B32B 2305/20* (2013.01); *B32B 2307/402* (2013.01); *B32B 2307/4023* (2013.01); *B32B 2307/50* (2013.01); *B32B 2307/54* (2013.01); *B32B 2307/58* (2013.01); *B32B 2307/726* (2013.01); *B32B 2307/7265* (2013.01); *B32B 2307/75* (2013.01); *B32B 2555/00* (2013.01); *B32B 2555/02* (2013.01); *Y10T 156/1052* (2015.01); *Y10T 156/1074* (2015.01); *Y10T 156/1075* (2015.01); *Y10T 156/1089* (2015.01); *Y10T 156/13* (2015.01); *Y10T 156/1322* (2015.01)

(56) References Cited

U.S. PATENT DOCUMENTS

| | | |
|---|---|---|
| 4,463,045 A | 7/1984 | Ahr et al. |
| 4,556,146 A | 12/1985 | Swanson et al. |
| 4,589,876 A | 5/1986 | Van Tilburg |
| 4,687,478 A | 8/1987 | Van Tilburg |
| RE32,649 E | 4/1988 | Brandt et al. |
| 4,834,735 A | 5/1989 | Alemany et al. |
| 4,950,264 A | 8/1990 | Osborn, III |
| 5,009,653 A | 4/1991 | Osborn, III |
| 5,267,992 A | 12/1993 | Van Tilburg |
| 5,625,222 A | 7/1997 | DesMarais et al. |
| 5,900,109 A * | 5/1999 | Sanders ............ A61F 13/15699 156/291 |
| 5,900,190 A | 5/1999 | Evans et al. |
| 6,004,893 A | 12/1999 | Van Tilburg |
| 6,623,464 B2 | 9/2003 | Bewick-Sonntag et al. |
| 7,967,801 B2 | 6/2011 | Hammons et al. |
| 8,058,501 B2 | 11/2011 | Hammons et al. |
| 8,292,864 B2 | 8/2012 | Hood et al. |
| 8,262,633 B2 | 9/2012 | Larson et al. |
| 8,691,041 B2 | 4/2014 | Oetjen |
| 2010/0036352 A1 | 2/2010 | Hood |
| 2011/0086780 A1 | 4/2011 | Colston, Jr. et al. |

OTHER PUBLICATIONS

All Office Actions for U.S. Appl. No. 14/189,374, filed Feb. 25, 2014.

All Office Actions for U.S. Appl. No. 12/908,519, filed Oct. 20, 2010.

\* cited by examiner

METHOD OF PRODUCING A COMPOSITE MULTI-LAYERED PRINTED ABSORBENT ARTICLE

FIELD OF THE INVENTION

Disclosed is a method for producing an absorbent article having multiple layers, wherein at least one of the layers is a composite.

BACKGROUND OF THE INVENTION

Composites of webs, such as films and fibrous webs are used in absorbent articles. For example, nonwoven webs are often combined with polymer films such that they are useful as materials in absorbent articles, such as backsheets on disposable absorbent diapers. In such composites the nonwoven portion can provide softness while the film portion can provide for fluid impermeability.

Composites in which nonwoven fibers protrude through a polymer film can be useful for providing an absorbent structure in which the nonwoven acts as the conveyor of fluid from one side of the polymer film to the other. The composite can be structured such that the fluid collecting side of the composite is the polymer film and nonwoven fibers protrude through the polymer film to the fluid collecting side of the composite. For example, in a sanitary napkin or diaper, such a composite can be practical for use as a topsheet that transports fluid from the body facing surface of the sanitary napkin more deeply into the sanitary napkin towards the absorbent core. If a composite is used in an absorbent article, such as a sanitary napkin, diaper, or tampon, this may result in the retained fluid appearing as a stain on the body facing surface of the composite. Stains of menses, vaginal discharge, urine, and feces may not be viewed favorably by the wearer of the absorbent article.

Colored regions have been used to help mask absorbed bodily fluid, for instance menses or urine, collected by absorbent articles. The ability to mask the absorbed bodily fluids provides a wearer with an increased feeling of cleanliness and protection from soiled undergarments. Further, a colored region positioned in a secondary layer of the central region of an absorbent article, provides a desired visual impression of depth to a wearer. This perception of absorbent article depth increases a wearer's confidence in the absorption capacity of the absorbent article, resulting in increased confidence that bodily fluids will be successfully absorbed and stored; thereby reducing the chance of soiled undergarments.

However it has been difficult to produce absorbent articles having the desired colored regions. One of the difficulties has been providing the central region of an absorbent article with a colored region that will provide the desired coverage; as some wearers associate stain patterns that extend outside the central colored region as indicating that the absorbent capacity of the absorbent article is exhausted. In some absorbent articles, the central colored region could account for less than 25% of the absorbent capacity of the absorbent article. Most digital printers lack the width-wise spray area to provide the desired colored region width to the central region, especially if products are produced multi-lane or broad front, where two or more products are simultaneously on the production line. One attempted fix has been to try and arrange multiple digital printers in a side-by-side arrangement to provide increased spray area in the widthwise direction of the absorbent article. The rearrangement of the digital printers has not provided the desired results. The side-by-side arrangement increases the cost of the digital printers and further decreases the reliability of the printing process. If one of the coupled printheads in the width direction fails, the production line stops. Image quality is also at risk as the multiple digital printers must be coordinated to produce a colored region that is not noticeably offset in the machine direction. As the colored region is on or close to the absorbent article surface any errors are quickly noticed by a wearer, reducing or eliminating the benefits provided by colored regions.

Another attempt to provide colored regions having the desired coverage area has been to use a contact method of printing, such as flexographic printing. Contact printing has traditionally been an economical way to print large or wide patterns on an absorbent article with reproducible results. However, contact printing may result in higher initial expense because the specific pattern rolls, plates, or screens must be manufactured. Because of the custom manufacturing, subsequent changes to the print pattern may require the manufacture of new equipment and may limit the economic feasibility of quickly changing the print pattern for specific needs or limited production situations. A further issue is that contact printing does not work equally well with all substrates. For example, to create the visual perception of depth the central portion will be printed on to create a central colored region. However to create the visual perception of depth, a layer below the surface layer (top layer) is printed to produce the central colored region. In general the layers below the surface layer include "dusty" or "loose" nonwoven or cellulose containing web materials that cannot be printed on using a contact method, as the loose fiber sticks to the print plate resulting in light or missing print.

In a further effort to provide the desired colored regions to an absorbent article, multiple printing processes have been used during the production of an absorbent article. These multiple printing processes have several shortcomings. In one method a single layer is printed on multiple times. However, printing on a single layer of an absorbent article multiple times does not provide a perception of depth that printing on multiple layers does. Another method involves printing on multiple layers of an absorbent article after they have been brought in contact with one another. This reduces the surfaces which can be printed, restricting printed webs to being in contact with one another, thus the perception of depth is lost. An additional method uses preprinted rolls of materials to produce absorbent articles. However the use of preprinted rolls increases the cost of the absorbent articles due to supply chain complexity and increased product scrap linked to registration of the image(s) in the preprinted roll.

Therefore there is a need for a method of producing absorbent articles having colored regions on multiple layers, one of which is a composite layer, such that the colored regions provide a visual perception of depth and sufficient coverage to at least partially mask absorbed bodily fluids.

SUMMARY OF THE INVENTION

A method of producing a multi-layered absorbent article having two or more colored regions is provided. The method comprises the steps of providing an absorbent article converting line; supplying a first precursor web to the converting line; printing a first colored region to the first precursor web using contact printing at a contact printing station; supplying a second precursor web to the converting line; producing a composite substrate from the first and second precursor webs; supplying a lower substrate to the converting line; printing a second colored region to the lower substrate using non-contact printing at a non-contact printing station; and combining the composite substrate having a first colored region with the lower substrate having a second colored region to produce an absorbent article.

A method of producing a multi-layered absorbent article having two or more colored regions is provided. The method comprises the steps of providing an absorbent article converting line; supplying a precursor film web to the converting line; printing a first colored region to the precursor film web using contact printing at a contact printing station; supplying a precursor non-woven web to the converting line; producing a composite substrate from the precursor film web and the precursor non-woven web; supplying a non-woven web material; printing a second colored region to the non-woven web material using non-contact printing at a non-contact printing station; cutting the composite substrate into individual sheets; cutting the non-woven web material into individual sheets; and combining an individual sheet of composite substrate and an individual sheet of non-woven material to produce an absorbent article.

DETAILED DESCRIPTION OF THE INVENTION

The present invention relates to a method of producing a printed multi-layered absorbent article on a converting line. A first precursor web is supplied to a converting line and printed with a first colored region using a contact method of printing, for instance, flexographic printing, rotogravure printing, offset printing, lithographic printing, screen printing, or the like. The first precursor is then combined with a second precursor web to form a composite substrate, such as a topsheet. A lower substrate, such as a non-woven or cellulose based secondary topsheet is also supplied to the converting line and printed with a second colored region using a non-contact method of printing, such as, for example, wax jet printing, ink jet printing, bubble jet printing, laser jet printing, or the like. Following the printing steps the composite substrate and lower substrate are combined in the process of producing an absorbent article, such as a feminine sanitary napkin.

As used herein the term "converting line" means a manufacturing line used to make absorbent articles. The purpose of a converting line is to take raw materials, process and combine them to produce absorbent articles. A converting line comprises various unit-operations used in the production of absorbent articles. A unit-operation can range from simple actions such as raw material transport (unwind, meter, reposition, and the like) to complex material transformations (melting, cutting, stretching, fluid application (ink, lotion, adhesive), and the like). In the converting line many unit-operations are occurring in parallel as well as in sequence to produce an absorbent article.

As used herein, the term "print" or "printing" means to produce a colored region on a substrate. Frequently, printing involves formation of a colored region by the transfer of pigment, colorant, or brightener in the form of ink, wax, paint, or the like to a substrate. The printed colored region is visible to the human eye and can include, for example, shapes, patterns, designs, objects, likenesses of real or fictitious characters, or the like, or combinations thereof. Examples of printing methods include contact printing and non-contact printing. Contact printing includes the direct transfer of pigment from a print roll, plate, or screen to a substrate. In non-contact printing methods, the printing apparatus does not directly contact the substrate, for example when printing from ink jet printers, wax jet printers, bubble jet printers, laser jet printers, or the like, or combinations thereof.

As used herein, the term "substrate" means a web of material capable of moving through a converting line. A substrate can include contiguous material wherein individual units of material are connected or directly joined to the immediately preceding and trailing units of material. For example, a substrate may include a continuous web of woven material, nonwoven material, film, or the like, or combinations thereof. A substrate may also include interconnected absorbent articles in various stages of manufacture. A substrate may also include a web of discrete units of material separated by space or by other materials. For example, a substrate may include discreet absorbent articles moving through a converting line via one or more conveyor belts or other means of conveyance known in the art.

As used herein, the phrase "absorbent article" refers to devices which absorb and contain fluids, which includes bodily fluids, and more specifically refers to devices which may be placed against or near the skin to absorb and contain the various fluids discharged from the body. In typical use absorbent articles are not intended to be laundered or otherwise restored or reused after a single use. Examples of absorbent articles include, but are not limited to sanitary tissue products, for example facial tissue, toilet tissue, paper towels, wipes; home care products, for example cleaning wipes, such as Swifter® (The Procter & Gamble Company, Cinc., Ohio); beauty care products such as wipes and cleaning pads; feminine hygiene products, for example sanitary napkins, pantiliners, tampons, interlabial devices and the like; infant diapers; children's training pants; adult incontinence products. Non-limiting examples of pantiliners and sanitary napkins which may be provided with a first colored region on a composite substrate and second colored region on a lower substrate include those manufactured by The Procter & Gamble Company of Cincinnati, Ohio, such as ALWAYS ULTRA, ALWAYS INFINITY, and ALWAYS pantiliners. Absorbent articles such as those disclosed in U.S. Pat. Nos. 4,324,246, 4,463,045, 6,004,893, 4,342,314, 4,463,045, 4,556,146, 4,589,876, 4,687,478, 4,950,264, 5,009,653, 5,267,992, and Re. 32,649 are also contemplated as being absorbent articles that might benefit from a first and second colored region.

Absorbent articles, and their individual components, such as a liquid pervious topsheet, a secondary topsheet, an absorbent core, and a substantially liquid impervious backsheet, have a body facing surface and a garment facing surface. As used herein, "body-facing surface" means that surface of the article or component which is intended to be disposed toward or placed adjacent to the body of the wearer during ordinary use, while the "garment facing surface" is on the opposite side, and is intended to be disposed to face away from the wearer's body during ordinary use. The garment facing surface may be arranged to face toward or placed adjacent to the wearer's undergarments when the absorbent article is worn. In general the topsheet is operatively permeable to the liquids that are intended to be held or stored by the absorbent article, and the backsheet may be substantially impermeable or otherwise operatively impermeable to the intended liquids. The absorbent article may also include components such as liquid wicking layers, liquid distribution layers, barrier layers, and the like, as well as combinations thereof.

The term 'color' as referred to herein includes any primary color, for example, white, black, red, blue, violet, orange, yellow, green, and indigo as well as any declination thereof or mixture thereof. The term 'non-color' or 'non-colored' refers to the color white which is further defined as those colors having an L* value of at least 80, an a* value equal to 0±2, and a b* value equal to 0±2.

Figure 1:
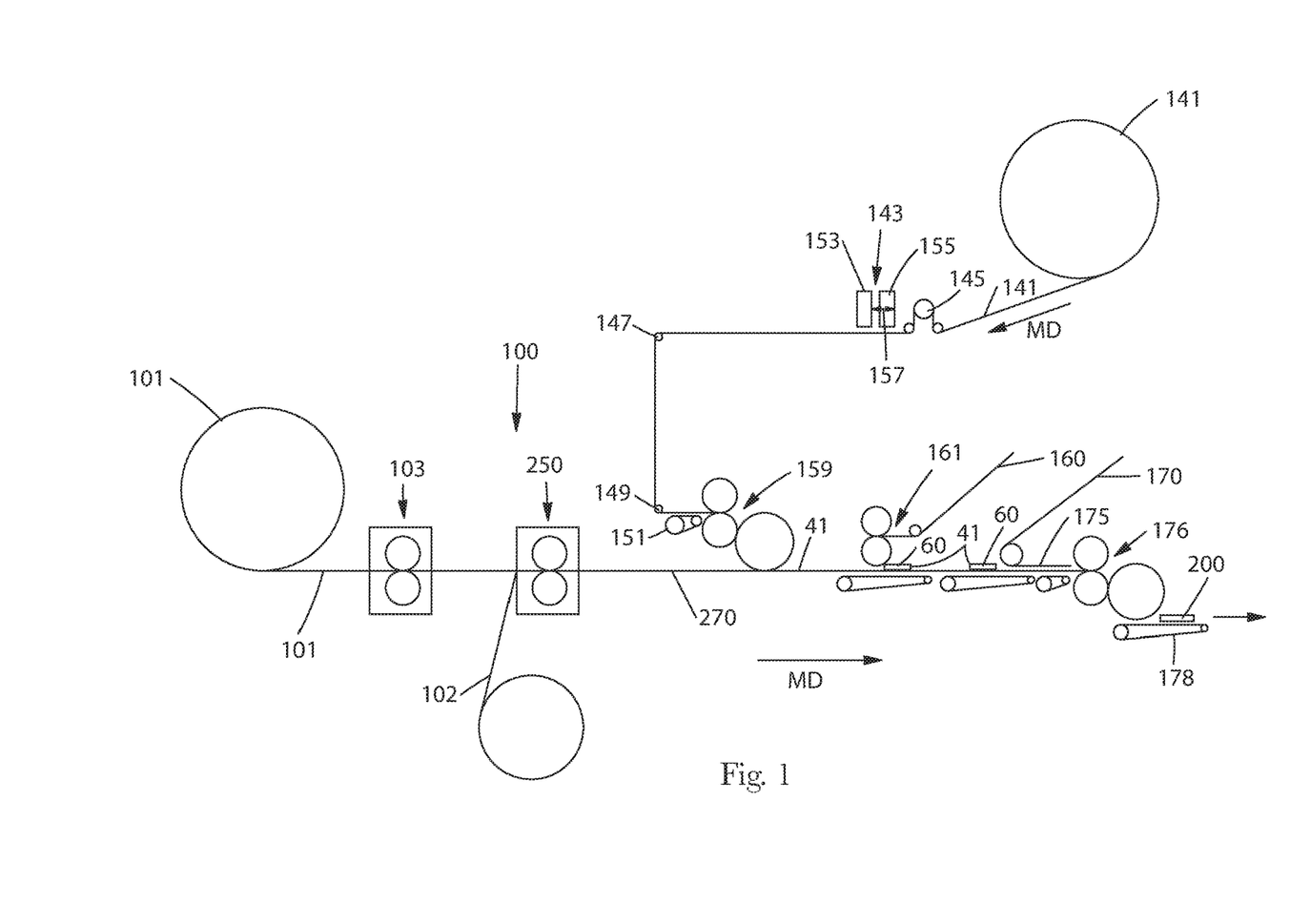
FIG. 1 is a schematic representation of one embodiment of the present invention.

One embodiment of the method is illustrated in FIG. 1, which shows a schematic representation of a converting line 100 according to the method of the present invention, wherein a first precursor web 101 is supplied to a contact printing station 103 within the converting line 100. The contact printing station 103 prints at least one first colored region on the first precursor web 101. The first precursor web 101 is then combined with a second precursor web 102 at a combination apparatus 250 within the converting line 100 to form a composite substrate 270. A lower substrate 141 is also supplied to a non-contact printing station 143 within the converting line 100. The non-contact printing station 143 prints at least one second colored region on the lower substrate 141. The first precursor web 101, second precursor web 102, and lower substrate 141 may be supplied to the converting line 100 concurrently.

With reference to FIG. 1 the method of the present invention can have a machine-direction (MD) which extends longitudinally, and a lateral cross-direction (CD) which extends transversely. The machine-direction is the direction along which a particular substrate is transported along and through a particular position of the converting line. The cross-direction lies generally within the plane of the substrate being transported through the converting line, and is aligned perpendicular to the machine-direction.

Figure 2:
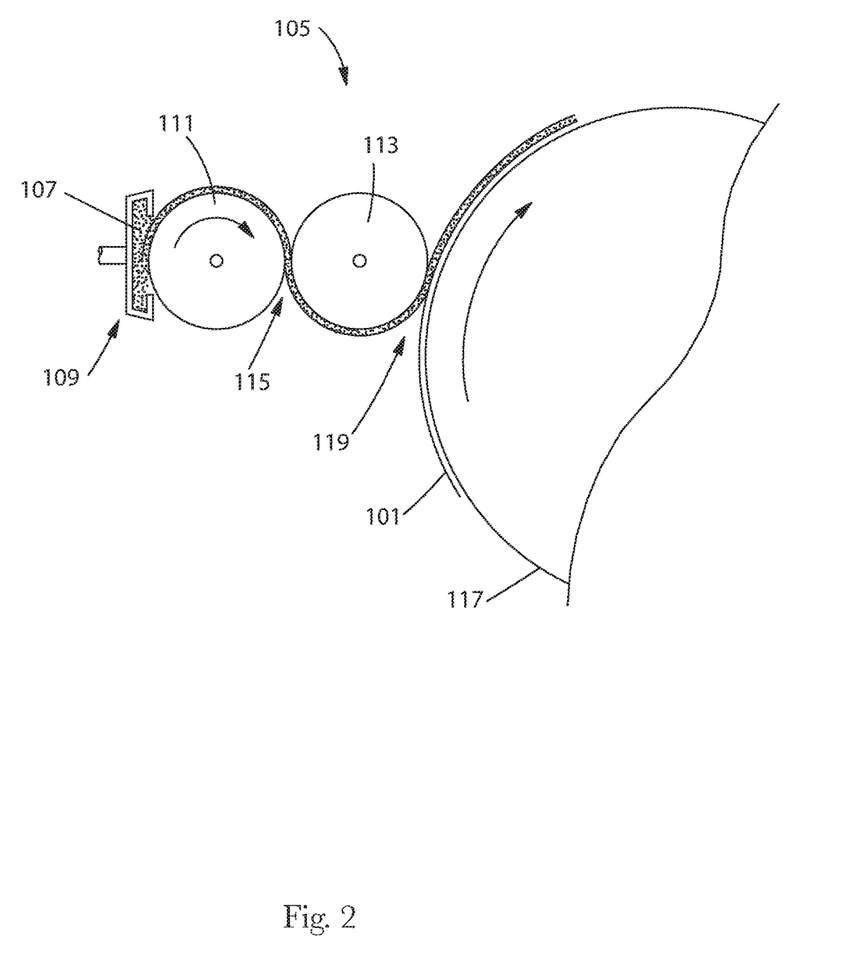
FIG. 2 is a schematic representation of a flexographic printing process of the present invention.

In one embodiment, the contact printing station 103 for printing a first colored region on a first precursor web 101 can comprise a flexographic printing process 105, as shown in FIG. 2. A flexographic printing process 105 can use any known flexographic printing apparatus and equipment, including processing means known in the art. As shown, ink 107 is supplied in a chamber 109 comprising a doctor blade, and which is in operative relationship with an anilox roller 111 to which ink 107 from the chamber 109 is transferred in a uniform manner as the anilox roller 111 rotates in the direction indicated. The anilox roller 111 is in operative relationship with a plate roller 113 such that at a transfer nip 115, ink 107 is transferred from the anilox roller 111 to the plate roller 113. The plate roller 113 picks up ink 107 from the anilox roller 111 in a pattern corresponding to the first colored region printed on a first precursor web 101. The first precursor web 101 on which the first colored region will be printed is fed onto the central impression drum 117 (in any conventional manner), which is rotating in the direction shown in FIG. 2.

As the first precursor web 101 enters the printing nip 119 formed by the operational relationship of the surfaces of the plate roller 113 and the central impression roller 117, the ink 107 on the surface of the plate roller 113 makes contact with, and is transferred to, the first precursor web 101.

Figure 3:
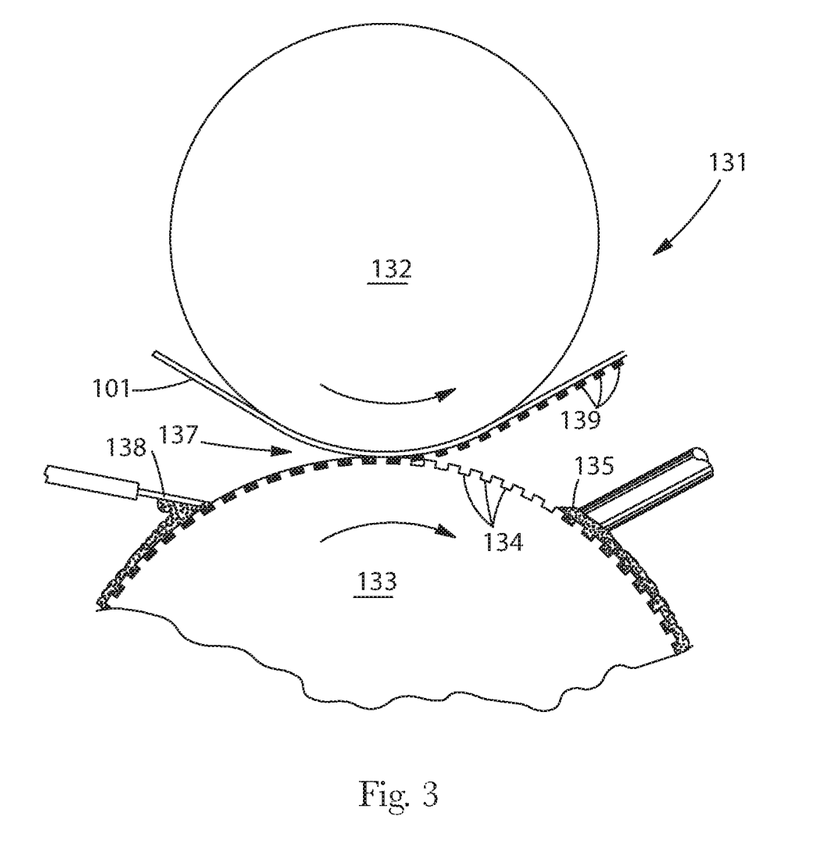
FIG. 3 is a schematic representation of a gravure printing process of the present invention.

Alternatives to the described flexographic printing process can also be used in the contact printing station of the present invention. For example, in certain embodiments, the contact printing station may comprise a gravure printing process 131 as illustrated in FIG. 3. In the gravure process 131, a first precursor web 101 is passed between a rubber impression roller 132 and a gravure cylinder 133. The surface of the gravure cylinder 133 contains a large number of cells 134, which are designed to receive, hold, and transfer ink to the first precursor web 101. Ink 135 is applied to the surface of the gravure cylinder 133 downstream of a nip 137 and is removed from the land areas of the gravure cylinder 133 with a doctor blade 138. As the first precursor web 101 enters the nip 137, it is pressed against the gravure cylinder 133 by the rubber impression roller 132, thereby permitting the ink 135 to transfer from the gravure cylinder cells 134 and be deposited on the surface of the substrate 101 in small colored or brightened areas 139 corresponding to the individual gravure cylinder cells 134.

Figure 4:
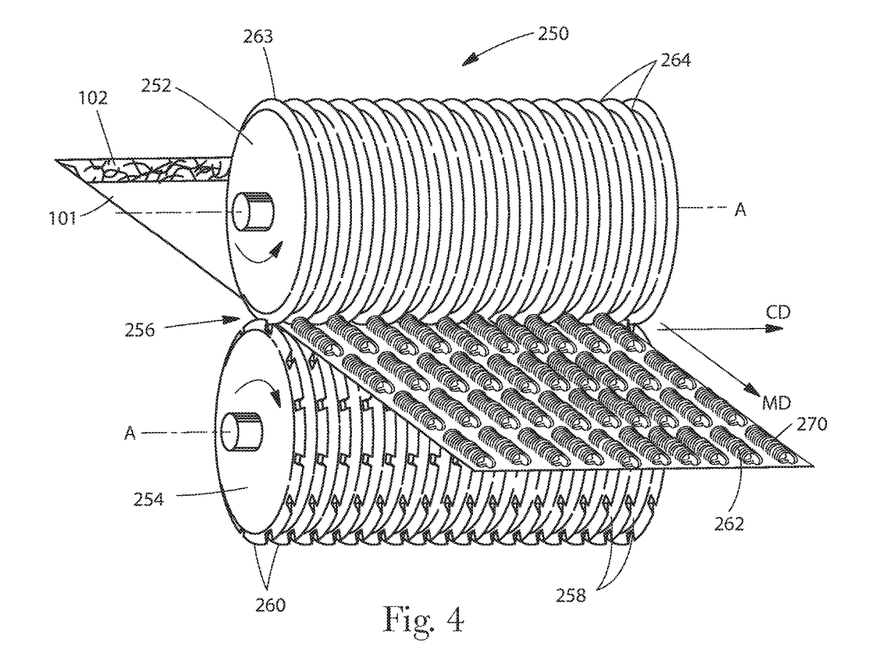
FIG. 4 is a perspective view of a combination apparatus used in the present invention.

As shown in FIGS. 1 and 4, following contact printing, the first precursor web 101 and a second precursor web 102 are moved in the MD to the nip 256 of counter-rotating interlocking rolls 252, 254 of the combination apparatus 250. The precursor webs 101, 102 may be held in sufficient web tension so as to enter the nip 256 in a generally flattened condition by means known in the art of web handling. As each precursor web 101, 102 goes through the nip 256, the teeth 260 of the patterned roll 254 interlock with the grooves 258 of the non-patterned grooved roll 252 to force portions of the second precursor web 102 out of the plane of the second precursor web 102, and through the plane of the first precursor web 101 to form tufts 262. The teeth 260 "push" or "punch" fibers of second precursor web 102 through the plane of first precursor web 101.

As shown in FIG. 4, in certain embodiments the combination apparatus 250 comprises a pair of interlocking rolls 252, 254, each rotating about an axis A, the axes A being substantially parallel in the same plane. Non-patterned grooved roll 252 comprises a plurality of ridges 263 and corresponding grooves 264 which extend unbroken around the entire circumference of the non-patterned grooved roll 252. The patterned roll 254 comprises a plurality of rows of circumferentially-spaced teeth 260, forming a pattern, that extend over at least a portion of patterned roll 254. The individual rows of teeth 260 are separated by corresponding grooves 258. In operation, non-patterned grooved roll 252 and patterned roll 254 interlock such that the ridges 263 of non-patterned grooved roll 252 extend into the grooves 258 of patterned roll 254; and the teeth 260 of patterned roll 254 extend into the grooves 264 of non-patterned grooved roll 252. The non-patterned grooved roll 252, patterned roll 254, or both can be heated by means known in the art, such as by using hot oil filled rollers or electrically-heated rollers.

In FIG. 4, the combination apparatus 250 is shown in a configuration having one patterned roll 254, and one non-patterned grooved roll 252. However, in certain embodiments two patterned rolls 254 may be used, each patterned roll 254 having either the same or differing patterns of teeth 260, in the same or different corresponding regions of the respective rolls. Such a combination apparatus can produce webs with tufts 262 protruding from both sides of the composite substrate 270. In certain embodiments the teeth 260 of the patterned roll 254 correspond to a colored region printed on the first precursor web 101, such that the tufts 262 produced in the composite substrate 270 correspond to the first colored region printed on the composite substrate 270. The first colored region helps mask the fluid absorbed by the second precursor web 102 of the composite substrate 270.

Figure 5:
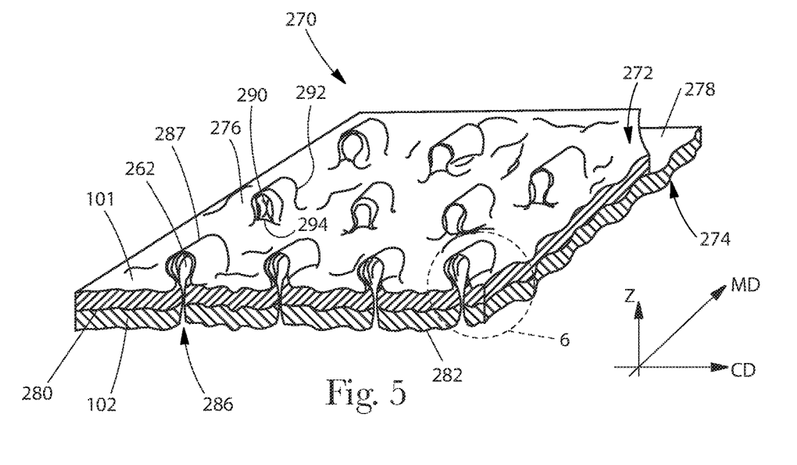
FIG. 5 is a perspective view of a composite substrate.

FIG. 5 shows a composite substrate 270 comprising generally planar, two-dimensional precursor webs, such as second precursor web 102 and first precursor web 101. Second precursor web 102 may be a fibrous nonwoven web and first precursor web 101 may be a polymer film. The precursor webs 101, 102 (and any additional webs) can be joined by adhesive, thermal bonding, ultrasonic bonding and the like. As disclosed above, the precursor webs 101, 102 of composite substrate 270 can be joined by intertwining mechanical engagement resulting from the formation of tufts 262. A representative tuft 262 for the embodiment of the composite substrate 270 shown in FIG. 5 is shown in a further enlarged view in FIG. 6. A tuft can be a plurality of raised loops of fibers or a pile of fibers integral with and out of plane of the web from which the loops or pile extend.

Composite substrate 270 has a first side 272 and a second side 274, the term "sides" being used in the common usage of generally planar two-dimensional webs, such as paper and films that have two sides when in a generally flat condition. Each precursor web 101, 102 has a first surface 276 and 278, respectively, and a second surface 280 and 282, respectively (shown in FIG. 5). The first surfaces 276 and 278 can be body facing surfaces and the second surfaces 280 and 282 can be garment facing surfaces. Composite substrate 270 has a machine direction (MD), a cross machine direction (CD), and an out of plane Z-direction, as is known in the art of web manufacture.

Figure 6:
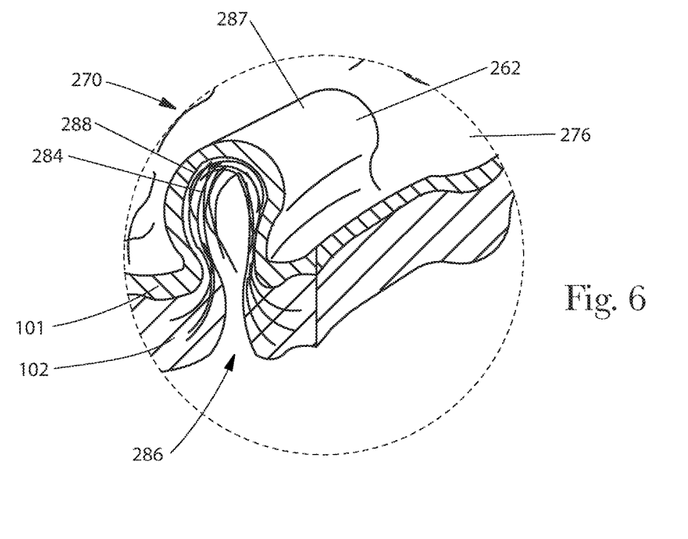
FIG. 6 is an enlarged view of a portion of the composite substrate shown in FIG. 5.

In one embodiment, the first side 272 of composite substrate 270 is defined by exposed portions of the first surface 276 of the first precursor web 101 and at least one, but in certain embodiments a plurality of, discrete tufts 262 which are integral extensions of the fibers of a nonwoven second precursor web 102. As shown in FIG. 6, each tuft 262 can comprise a plurality of looped, aligned fibers 284 extending through the first surface 276 of the first precursor web 101 and outwardly from the first surface 276 thereof The second precursor web 102 can be a fibrous woven or nonwoven web comprising fibers having sufficient elongation properties to have portions formed into tufts. For example, in certain embodiments a second precursor web 102 can be a fibrous woven or nonwoven web comprising elastic or elastomeric fibers, for instance natural fibers, such as wood or cotton fibers; synthetic fibers, such as polymeric fibers—for example polyester, polypropylene, or polyethylene fibers; or from a combination of natural and synthetic fibers. Elastic or elastomeric fibers can be stretched at least about 50% and return to within 10% of their original dimension. Tufts 262 can be formed from elastic fibers if the fibers are simply displaced due to the mobility of the fiber within the nonwoven, or if the fibers are stretched beyond their elastic limit and are plastically deformed. In certain embodiments tufts are formed by moving fibers out-of-plane in the Z-direction at discrete, localized, portions of the second precursor web 102. The moving out-of-plane can be due to fiber displacement, that is, the fiber is able to move relative to other fibers and be "pulled" out-of-plane. In certain embodiments, however the fibers of the non-woven second precursor web 102 are at least partially stretched out-of-plane and permanently deformed to produce tufts 262. Therefore, in one embodiment, depending on the desired height of tufts 262, the constituent fibers of a nonwoven second precursor webs 102 can exhibit an elongation to break of at least about 5%, of at least about 10%, of at least about 25%, of at least about 50%, or of at least about 100%. Elongation to break can be determined by simple tensile testing, such as by use of Instron tensile testing equipment, and can generally be found on material data sheets from suppliers of such fibers or webs.

First precursor web 101 can be a polymer film web having sufficient integrity to be formed into the composite by the process described above, for example apertured formed thermoplastic films, apertured plastic films, hydroformed thermoplastic films, and reticulated thermoplastic films. In certain embodiments the first precursor web 101 may have sufficiently less elongation properties relative to the second precursor web 102, such that upon experiencing the strain of fibers from second precursor web 102 being moved out-of-plane in the direction of first precursor web 101, first precursor web 101 will rupture, for example by tearing due to extensional failure, such that portions of second precursor web 102 can extend through the plane of the first surface 276 of first precursor web 101 to form tufts 262 on first side 272 of composite substrate 270 and a cap 287 will remain over the distal portion of each tuft 262.

As shown in FIGS. 5 and 6 tufts 262 extend above openings 286 in the first precursor web 101. The openings 286 are formed by locally rupturing the first precursor web 101 by the process described above. Rupture may involve a simple splitting open of the first precursor web 101, such that a portion or portions of first precursor web 101 can be deflected or moved out-of-plane (the plane of first precursor web 101) to form cap structures, referred to herein as a cap, or caps, 287. Caps 287 are integral extensions of the first precursor web 101, which may be a polymer film. The form and structure of caps 287 may be dependent upon the material properties of the first precursor web 101. In certain embodiments at least part of a distal portion 288 of each of the tufts 262 is covered by a cap 287. A cap 287 can be a tunnel shaped cap 287 having a first opening 290 and a second opening 292. The first opening 290 comprises a location of rupture 294 in the first precursor web 101 and the tuft 262 extends above the location of rupture 294. A cap 287 is formed by rupturing the first precursor web 101 in at least one location of rupture 294 and stretching the polymer film out of plane of the first surface 276 of the first precursor web 101 to form an opening such as a first opening 290 or a first opening 290 and a second opening 292. The location of rupture 294 can define at least part of the boundary of the opening 286. The first precursor web 101 can be fluid impervious in the absence of a rupture 294.

As shown in FIG. 1, in the method of the present invention the converting line 100 also comprises a non-contact printing station 143. The non-contact printing station 143 may use a non-contact process to print at least one second colored region on a lower substrate. In one embodiment the non-contact printing station 143 may include an inkjet process. In this embodiment the non-contact printing station 143 includes an inkjet printing station capable of printing a colored region on a lower substrate 141, such as a nonwoven or cellulose based web for use as a secondary topsheet. The lower substrate 141 can be provided to the non-contact printing station 143 by any suitable means; for example as shown in FIG. 1, through the use of a first metering device 145 (for example an omega roll or an s-wrap device), a series of idle rollers 147 and 149, and a second metering device 151 (for example a vacuum conveyor). Both the metering devices 145 and 151 create a desired tension in the lower substrate 141 and move the lower substrate 141 in a machine direction MD at a desired linear velocity V, which can be as high as about 10 meters/ second or even greater. However, the present invention is applicable at any other linear velocity V of the lower substrate, for example, at least 5 meters/second, at least 4 meters/second, at least 3 meters/second, at least 2 meters/ second, and lower (which occurs during a startup of the converting line when the converting line speed, including the linear velocity V of the lower substrate 141, is gradually increasing from a zero to a desired production speed).

As shown in FIG. 1, the inkjet printing station 143 in certain embodiments may include a dual-head arrangement comprising a first inkjet print head 153 and a second inkjet print head 155, disposed at a spatial distance 157 extending in the machine direction MD. However, it should be noted that the first and the second print heads 153, 155 could be disposed from each other at any desired spatial distance. In certain embodiments the first inkjet print head 153 and second inkjet print head 155 can be oriented in a side-by-side manner in a cross-direction across the lower substrate. This side-by-side orientation increases the widthwise coverage of the inkjet print heads 153, 155.

The first and the second print heads 153 and 155 can be any type that is suitable to print a colored region, and may be disposed at a certain suitable distance from the lower substrate 141. In certain embodiments the distance may be form about 0.5 mm to about 3 mm, and in certain other embodiments from about 1 mm to about 2 mm. In certain embodiments, the inkjet printing station may comprise one or more digital printers, such as a continuous binary array allowing for a greater ink drop velocity than other inkjet printers, allowing for a wider gap between the print head and web to provide a quality image.

The print heads 153 and 155 can be supplied with ink from a common ink source; although in certain embodiments, separate ink sources can be also utilized.

Each of the print heads 153 and 155 includes a multiplicity of jets dispensing a multiplicity of substantially uniform ink dots. In one embodiment of the present invention, each of the print heads 153 and 155 can include 256 jets, forming a linear configuration in the cross-direction of about 2 inches long (about 50.8 mm). Therefore, each of the print heads 153 and 155 can print an ink image containing 256 ink dots extending linearly about 50.8 mm across the lower substrate 141. This arrangement is sufficient for printing any image of up to about 50.8 mm wide, as measured in the cross-direction of the lower substrate 141. However, any number of jets per a print head can be provided to print a desired width W of a colored region, which in certain embodiments, for absorbent articles produced in the process of the present invention can vary from about 5 mm to about 185 mm, in certain other embodiments from about 20 mm to about 105 mm.

With respect to the print heads having 256 jets, such print heads are available from Videojet Technologies, Inc., (Wood Dale, Ill.). The printing station 143 can be a part of an inkjet printing system that is also available from Videojet Technologies, Inc., as the BX6000 series inkjet print system including an ink source and a controller for providing ink and controlling jets forming individual ink droplets.

In the BX6000 series inkjet print system a continuous binary array can be used, wherein the ink droplets are dispensed from all of the jets of the print heads 153 and 155 continuously, but only certain ink droplets are allowed to reach the lower substrate 141 at desired locations to form a printed image. The other ink droplets can be prevented from reaching the lower substrate 141 by deflecting the ink droplets into a recycling flow for a continuous re-use. The operation of the individual ink jets of each print head can be controlled by a controller included in the BX6000 series system.

In certain embodiments, in place of a continuous type of the inkjet printing system the inkjet printing system can be an on-demand type inkjet printing system (such as thermal ink jet or Peizo Drop on Demand), wherein ink typically is not recycled and ink droplets are formed on a demand basis and in a desired order to print a colored region.

Referring again to FIG. 1, each of the first and the second print heads 153 and 155 is capable of printing colored regions separately from each other. For example, in certain embodiments when the first print head 153 is in a print mode, the second print head 155 can be in a standby or idle mode (is not printing an image on the lower substrate 141). Conversely, when the first print head 153 is in a standby mode, the second print head 155 can be in a print mode, printing an image. As described above, in both modes of operation, the print mode and the standby mode, the droplet formation by each of the 256 jets of each of the print heads 153 and 155 occurs continuously; however, in the standby mode, all of the dispensed droplets are deflected and recycled into a recycled ink flow, but in the print mode the un-deflected droplets are deposited on the lower substrate 141 and the deflected droplets are recycled into the recycle ink flow. In certain other embodiments, the first print head 153 and second print head 155 can print colored regions at the same time to print two colors. In another embodiment, the first print head 153 and second print head 155 can be offset in the CD to increase the CD resolution, for example from 128 dpi to 256 dpi. A still further embodiment the first print head 153 and second print head 155 can be used to print the same colored region twice to increase color intensity.

Referring again to FIG. 1, after the inkjet printing, the lower substrate 141 travels to a cut and placement device 159, capable of severing the lower substrate 141 into individual sheets comprising, in this embodiment the secondary topsheet 41, and then placing the secondary topsheets 41 at a desired pitch interval P onto a topsheet web 270 produced from the composite substrate 270 moving in a machine direction MD at a desired velocity. The topsheet web 270 can be provided and metered at a desired velocity by any suitable means known to one skilled in the art. Then, an absorbent core web 160 (which can be also provided and metered by any suitable means) is cut into individual absorbent cores 60, which are then placed onto a secondary topsheet 41, previously disposed on the topsheet web 270. The cutting and placing operations of the absorbent core 60 can be provided by a cut-and-slip or cut-and-lay device 161 or any suitable web cutting and placing device known in the art. Further, a backsheet web 170 (which can be also provided and metered by any suitable means) is deposited onto the absorbent cores 60 to provide a sandwiched-type web 175, which is subsequently bonded together and cut into individual absorbent articles 200. The bonding, cutting, and placing operations of the sandwiched-type web 175 can also be provided by any suitable means known in the art, for example, by a final knife 176. A variety of suitable securing mechanisms or systems known to one of skill in the art may be utilized to achieve any bonding. Examples of such securing mechanisms can include, but are not limited to, the application of adhesives in a variety of patterns between the two adjoining surfaces, entangling at least some portions of one absorbent body component with portions of the adjacent surface of another component, or fusing at least portions of the adjacent surface of one component to portions of another component of the absorbent. The individual absorbent articles, which in this instance are feminine sanitary napkins 200, can then be transported by any suitable means, such as a conveyor 178, to other downstream operations, such as folding, wrapping, and packing.

Figure 7:
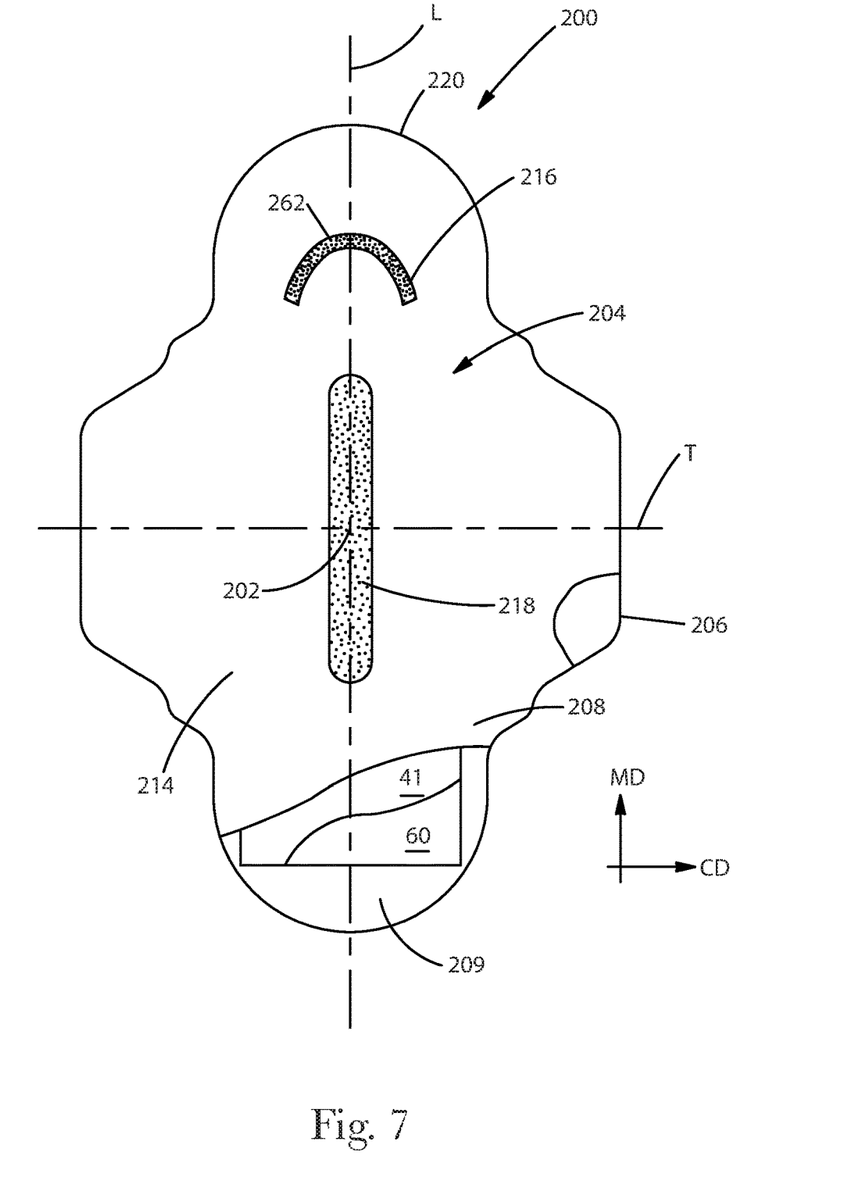
FIG. 7 is a schematic of an absorbent article.

Referring now to FIG. 7, a top view of an absorbent article produced from the method of the present invention is shown, which in this illustrated embodiment is a feminine sanitary napkin 200. The feminine sanitary napkin 200 can have a substantially planar configuration and a central region 202. The central region 202 is the in-plane center of mass of the feminine sanitary napkin 200. The central region 202 is at the intersection between the longitudinal centerline L and transverse centerline T. The transverse centerline T is perpendicular to the longitudinal centerline L. The feminine sanitary napkin 200 can be symmetrical or asymmetrical about the transverse centerline T. The feminine sanitary napkin 200 has a body facing surface 204 comprising a topsheet 208 produced from a composite substrate, an absorbent core 60, a secondary topsheet 41 produced from a lower substrate positioned between the topsheet 208 and absorbent core 60, and a garment facing surface 206 comprising a liquid impervious backsheet 209.

In certain embodiments the secondary topsheet may be compliant, soft feeling, and non-irritating to the wearers skin and hair. Further, the secondary topsheet is liquid pervious, permitting liquids, such as menses or urine, to readily penetrate through its thickness. A suitable secondary topsheet may be manufactured from a wide range of materials such as woven and nonwoven materials, for example a nonwoven web of fibers; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of: natural fibers, such as wood or cotton fibers; synthetic fibers, such as polymeric fibers—for example polyester, polypropylene, or polyethylene fibers; or from a combination of natural and synthetic fibers. When the secondary topsheet comprises a nonwoven web, the web may be manufactured by a wide number of known techniques. For example, the web may be spunbonded, carded, wet-laid, melt-blown, hydroentangled, combinations of the above, or the like.

The backsheet is substantially impervious to liquids, such as menses or urine and may be manufactured from a thin plastic film, although other flexible liquid impervious materials may also be used. The backsheet prevents the exudates absorbed by the absorbent core from wetting a wearer's bedding or clothes, for example bedsheets, pants, pajamas and undergarments. In certain embodiments, the backsheet can operatively permit a sufficient passage of air and moisture vapor out of an absorbent article, particularly out of the absorbent core, while blocking the passage of bodily liquids. The backsheet may thus comprise: a woven or nonwoven material; polymeric films, such as thermoplastic films of polyethylene or polypropylene; or composite materials such as a film-coated nonwoven material. In one embodiment, the backsheet can be a breathable backsheet such as that described in U.S. Pat. No. 6,623,464 (Bewick-Sonntag et al.) issued 23 Sep. 2003.

As shown in FIG. 7 the backsheet 209 and the topsheet 208 are positioned adjacent the garment facing surface 206 and the body facing surface 204, respectively, of the absorbent core 60. In certain embodiments the absorbent core can be joined with the topsheet, the backsheet, or both by known attachment means, such as those described above or those well known in the art. However, in certain embodiments of the present invention the absorbent core is unattached to the topsheet, the backsheet, or both.

The absorbent core 60 in FIG. 1 is generally disposed between the topsheet 208 and the backsheet 209. The absorbent core 60 may comprise any absorbent material that is generally compressible, conformable, non-irritating to the wearer's skin, and capable of absorbing and retaining liquids such as urine and other certain body exudates, such as menses. The absorbent core 60 may comprise a wide variety of liquid-absorbent materials commonly used in feminine care articles and other absorbent articles, such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams such as foams formed from High Internal Phase Emulsions (HIPEs); absorbent sponges; superabsorbent polymers; absorbent gelling materials; or any other known absorbent material or combinations of materials. The absorbent core may further comprise minor amounts (typically less than 10%) of non-liquid absorbent materials, such as adhesives, waxes, oils and the like. Examples of absorbent structures that may be used in the present invention are found in U.S. Pat. No. 4,834,735 (Alemany et al.) issued 30 May 1989; U.S. Pat. No. 5,625,222 (DesMarais et al.) 22 Jul. 1997.

The absorbent core may also include one or more superabsorbent materials. Superabsorbent materials suitable for use in the present invention are known to those skilled in the art, and may be in any operative form, such as particulate form. The superabsorbent material can be a water-swellable, generally water-insoluble, hydrogel-forming polymeric absorbent material, which is capable of absorbing at least about 20, in certain embodiments about 30, and in additional embodiments about 60 times or more its weight in physiological saline (for example 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors, such as the Dow Chemical Company and Stockhausen, Inc. The superabsorbent material may be included in an appointed storage or retention portion of the absorbent article, and may optionally be employed in other components or portions of the absorbent article.

As shown in FIG. 7, the feminine sanitary napkin 200 can be considered to have a viewing surface that is the body facing surface 204. The topsheet 208 and secondary topsheet 41 are visible (can be visually perceived by the observer) when the body facing surface 204 is presented towards an observer even though the topsheet is between the observer and the secondary topsheet 41.

When the body facing surface 204 of the feminine sanitary napkin 200 is viewed, the feminine sanitary napkin 200 can have a background region 214. The background region 214 is a region that is visually distinguishable from the first colored region 216 and second colored region 218. The background region 214 can be white or any other color visually distinguishable from the first colored region 216 and second colored region 218. Colors are believed to be visually distinguishable if there is a □E between the two colors of at least about 1.

The topsheet 208 comprises the first colored region 216. The first colored region 216 can be the constituent color of the topsheet 208 with the background region 214 rendered to have a color that differs from the constituent color of the topsheet 208. The first colored region 216 can correspond to a pattern of tufts 262 formed in the topsheet 208. The first colored region 216 helps mask the absorbed bodily fluids that may be visible to a wearer due to retention of the absorbed bodily fluids by the second precursor web 102 of the topsheet 208 formed from a composite substrate 270. The first colored region 216 can be provided on, for instance, the body facing side of the topsheet 208 or the garment facing side of the topsheet 208. Similarly, the secondary topsheet 41 comprises the second colored region 218. The second colored region 218 can be the constituent color of the secondary topsheet 41 with the background region 214 rendered to have a color that differs from the constituent color of the secondary topsheet 41. The second colored region 218 can be provided on, for instance, the body facing side of the secondary topsheet 41 or the garment facing side of the secondary topsheet 41. The second colored region 218 can be coincident with the longitudinal centerline L. That is, a portion of the second colored region 218 can intersect with the longitudinal centerline L.

When the body facing surface 204 is viewed, the background region 214, first colored region 216, and second colored region 218 are viewable by an observer. The first colored region 216 and second colored region 218 are visibly distinct from the background region 214 in that first colored region 216 and second colored region 218 each differ in color as compared to the background region 214. The first colored region 216 and the background region 214 can differ in color by a □E, which is discussed in more detail below, of at least about 1. The first colored region 216 and the background region 214 can differ in color by a □E, which is discussed in more detail below, of at least about 3, if more visual distinctiveness is desired.

Similarly, the second colored region 218 and the background region 214 can differ in color by a □E of at least about 1. The first colored region 216 and the second colored region 218 can both differ in color as compared to the background region 214 by a □E of at least about 1. The first colored region 216 and the second colored region 218 can be more visually distinguishable if there is a □E between the two colors of at least about 3.

As shown in FIG. 7, in certain embodiments, the first colored region 216 can be laterally more extensive in a direction perpendicular to the longitudinal centerline L than the second colored region 218.

The first colored region 216 can be designed so as to be visually complementary to the second colored region 218 and be presented to the viewer over a wider/more extensive portion of the body facing surface 204. It is thought that by having the first colored region 216 on a different layer of material than the second colored region 218 that a richer visual impression can be created on the feminine sanitary napkin 200. For instance, since the first colored region 216 and second colored region 218 are on different layers of materials, when viewed, at least one of the colored regions will be viewed through the layer comprising the other colored region. A colored region viewed through another layer material can have a significantly different visual impression in terms of softness/diffuseness of the image, somewhat like the difference between a matte finished photograph versus a gloss finished photograph.

Further, if the second colored region 218 is provided by inkjet printing, the design of the second colored region 218 can be easily changed so that feminine sanitary napkins 200 within a single package or different packages can have different designs for the second colored region 218. The first colored region 216 might be provided by a contact printing apparatus that cannot be easily altered. Thus, the first colored region 216 can be a constant design recognizable by consumers as being a product from a particular brand or of a particular quality.

A first colored region 216 that is laterally more extensive than the second colored region 218 can also provide the impression to the wearer that such laterally more extensive portions of the feminine sanitary napkin 200 are capable of acquiring and retaining fluid. For instance, if the first colored region extends across a substantial portion of the feminine sanitary napkin 200 in the cross-direction CD, viewers of the feminine sanitary napkin 200 may interpret the first colored region 216 as providing a barrier to fluid flow beyond the first colored region 216 or a boundary beyond which the user should not expect fluid to pass as the fluid travels in the machine-direction MD of the feminine sanitary napkin 200.

The second colored region 218 can be coincident with the central region 202. The central region 202, being the in-plane center of mass of the feminine sanitary napkin 200, might be associated by the wearer as being the location of the feminine sanitary napkin 200 that should be proximal her vaginal opening or urethra. Designs in which the second colored region 218 is symmetric about the longitudinal centerline may provide for a more pleasing impression of the feminine sanitary napkin 200 than designs in which the second colored region 218 is not symmetric with respect to the longitudinal centerline L.

As shown in FIG. 7, the second colored region 218 and first colored region 216 can be spaced apart from one another along the longitudinal centerline. By spacing apart the first colored region 216 and second colored region 218, it is believed that improper phasing of the topsheet 208 and secondary topsheet 41 that might occur when the two substrates are brought together during manufacture might not be so apparent to the wearer because it might be difficult to perceive relatively small differences from one pad to another pad of a gap between the first colored region 216 and second colored region 218. The first colored region 216 and second colored region 218 can be separated from one another by the background region 214.

As shown in FIG. 7, the feminine sanitary napkin 200 has a periphery 220. The background region 214 can be between the first colored region 218 and the periphery 220. Such an arrangement is thought to provide for an improved visual impression in that the periphery 220 has a clean line that is not interrupted by colored regions of the feminine sanitary napkin 200. For the same reason, the first colored region 216 and second colored region 218 can be substantially surrounded by the background region 214. For instance, less than 25% of the periphery 220 can be interrupted by the second colored region 218 or first colored region 216 or the combination of the first colored region 216 and second colored region 218. The second colored region 218 can be surrounded by the background region 214.

The second colored region 218, as shown in FIG. 7, can be a substantially elongated shape. Without being bound by theory, it is believed that substantially elongated shapes that are aligned with or on the longitudinal centerline L may make the feminine sanitary napkin 200 look as if the feminine sanitary napkin 200 is slim as compared to a feminine sanitary napkin devoid of such an elongated shape. A wearer might associate such an impression with a belief that the apparently narrow feminine sanitary napkin 200 will fit comfortably in the crotch of their panty. The second colored region 218, in certain embodiments can have a width less than about 50% of the maximum distance between portions of the periphery 220 coincident with the transverse centerline T. Ovals and generally rectangular shaped shapes are examples of substantially elongated shapes. To provide for more visually coherent designs, the first colored region 216 and second colored region 218 can be within a CIELab color space volume of less than about 200. CIELab color space volume is discussed in more detail below. With such an approach, the colors of the first colored region 216 and second colored region 218 do not differ substantially to the eye of most viewers and viewers might perceive the colors to be the same or shades or subtle variations of the same color. Subtle variations in color are thought to be pleasing to the eye, much like sample paint chips having slightly varying colors found in home decoration stores that can be pleasurable and interesting to view. If less distinctiveness between the first colored region 216 and second colored region 218 is desired, the first colored region 216 and second colored region 218 can be within a CIELab color space volume of less than about 50.

The first colored region 216 can be substantially arcuate shaped. Arcuate shaped first colored regions 216 are thought to be perceived by wearers as barriers to flow of liquid in the absorbent article or as providing an indication to a wearer that they may not want fluid to pass beyond such a colored region or that once such fluid flow has occurred they may want to be prepared to wear a fresh product in the near future.

Arcuate shapes include, but are not limited to, shapes generally corresponding to those found on common keyboards including the greater than symbol, parenthesis, circumflex (also referred to as the caret symbol), and bracket as well as generally c-shaped shapes, and slight modifications of any of these previously mentioned shapes. Arcuate shapes, as defined herein, can be generally curved like a letter C or can be more angular such as the symbol <. Thus, arcuate shapes do not necessarily have any particular curvature.

Figure 8:
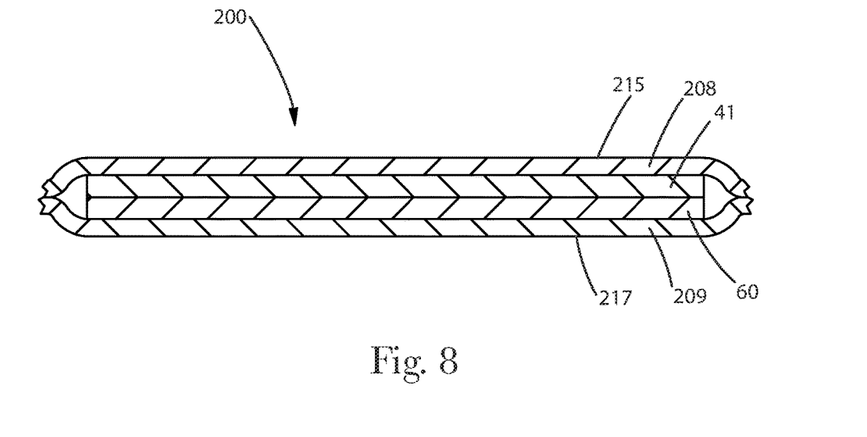
FIG. 8 is a cross-section of the absorbent article illustrated in FIG. 7.

A cross section of the feminine sanitary napkin 200 illustrated in FIG. 7 is shown in FIG. 8. Each component of the feminine sanitary napkin 200 can be considered to have a body facing side 215 and a garment facing side 217. The body facing side 215 being oriented towards the wearer's body when the absorbent article is in-use and the garment facing side 217 opposing the body facing side 215.

Figure 9:
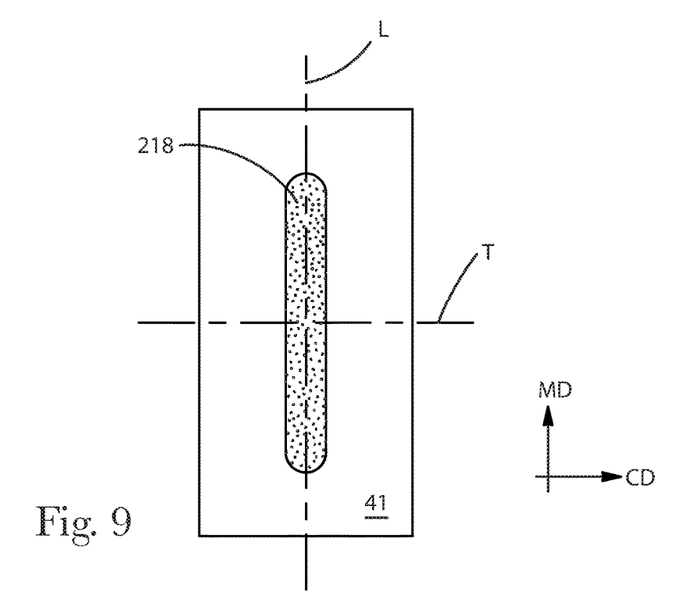
FIG. 9 is a schematic of the lower substrate of the absorbent article of FIG. 7.
Figure 10:
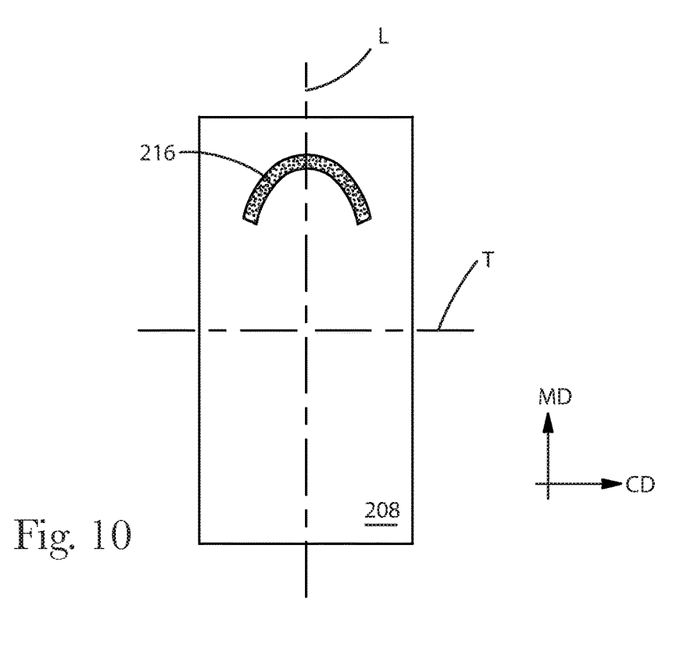
FIG. 10 is a schematic of the composite substrate of the absorbent article of FIG. 7.

FIG. 9 is a schematic of a secondary topsheet 41 of a feminine sanitary napkin having a second colored region 218. FIG. 10 is a schematic of a topsheet 208 of a feminine sanitary napkin having a first colored region 216. The secondary topsheet 41 illustrated in FIG. 9 can be registered with the topsheet 208 illustrated in FIG. 10 to create a feminine sanitary napkin 200 having a visual impression similar to that illustrated in FIG. 7.

The color of the first colored region 216 and second colored region 218 and background region 214 are measured by the reflectance spectrophotometer according to the colors L*, a*, and b* values. The L*, a*, and b* values are measured from the body facing surface 204 of the feminine sanitary napkin 200 inboard of the periphery 220 of the feminine sanitary napkin 200.

The difference in color is calculated using the L*, a*, and b* values by the formula $\Delta E=[(L^*_{X}-L^*_{Y})^2+(a^*_{X}-a^*_{Y})^2+(b^*_{X}-b^*_{Y})^2]^{1/2}$. Herein, the 'X' in the equation may represent the first colored region 216, the second colored region 218, or the background region 214 and 'Y' may represent the color of another region against which the color of such region is compared. X and Y should not be the same two points of measurement at the same time. In other words, for any particular comparison of the difference in color, the location of X≠ the location of Y.

Where more than two colors are used, the 'X' and 'Y' values alternately include points of measurement in them also. The key to the ΔE calculation herein is that the 'X' and 'Y' values should not stem from the same measured point on the viewing surface. In those instances where there is effectively no background region 214 within the confines of the measurement area, the 'X' values should flow from a point different in spatial relationship to the 'Y' values, but within the confines of the absorbent core periphery.

Reflectance color is measured using the Hunter Lab LabScan XE reflectance spectrophotometer obtained from Hunter Associates Laboratory of Reston, Va. A feminine sanitary napkin 200 is tested at an ambient temperature between 65° F. and 75° F. and a relative humidity between 50% and 80%.

The spectrophotometer is set to the CIELab color scale and with a D65 illumination. The Observer is set at 10° and the Mode is set at 45/0°. Area View is set to 0.125" and Port Size is set to 0.20" for films. The spectrophotometer is calibrated prior to sample analysis utilizing the black glass and white reference tiles supplied from the vendor with the instrument. Calibration is done according to the manufacturer's instructions as set forth in LabScan XE User's Manual, Manual Version 1.1, August 2001, A60-1010-862. If cleaning is required of the reference tiles or samples, only tissues that do not contain embossing, lotion, or brighteners should be used (e.g., PUFFS tissue). Any sample point on the absorbent article containing the imparted color to be analyzed can be selected.

The feminine sanitary napkin 200 is placed over the sample port of the spectrophotometer with a white clamp disk placed behind the feminine sanitary napkin 200. The feminine sanitary napkin 200 is to be in a substantially flat condition and free of wrinkles.

The feminine sanitary napkin 200 is removed and repositioned so that a minimum of six readings of color of the body facing surface 204 are conducted. If possible (e.g., the size of the imparted color on the element in question does not limit the ability to have six discretely different, non-overlapping sample points), each of the readings is to be performed at a substantially different region on the externally visible surface so that no two sample points overlap. If the size of the imparted colored region requires overlapping of sample points, only six samples should be taken with the sample points selected to minimize overlap between any two sample points. The readings are averaged to yield the reported L*, a*, and b* values for a specified color on an externally visible surface of an element.

In calculating the CIELab color space volume, V, maximum and minimum L*, a*, and b* values reported are determined for a particular set of regions to be measured. The maximum and minimum L*, a*, and b* values reported are used to calculate the CIELab color space volume, V, according to the following formula:

$$V = \frac{4}{3}\left|\frac{\Delta L^*}{2}\right|\left|\frac{\Delta a^*}{2}\right|\left|\frac{\Delta b^*}{2}\right|$$

Within the above formula, ΔL* is the difference in L* values between the two colored regions being compared and is calculated by: $\Delta L^* = L^*_X - L^*_Y$. The Δa* is the difference in a* values between the two colored regions being compared and is calculated by: $\Delta a^* = a^*_X - a^*_Y$. The Δb* is the difference in b* values between the two colored regions being compared and is calculated by: $\Delta b^* = b^*_X - b^*_Y$. The CIELab color space volume can result in a solid substantially ellipsoidal in shape. If ΔL*, Δa*, and Δb* are equal, the solid will be spherical. As used herein, a "solid" refers to the mathematical concept of a three-dimensional figure having length, breadth, and height (or depth). An ellipsoidal volume is preferred to calculate volume because an ellipsoid generally requires the dimensional differences of ΔL*, Δa*, and Δb* to be relatively more uniform than other solids. Furthermore, it is believed that ellipsoidal volumes are more visually acceptable (less detectable color mismatch by human perception) than spherical volumes.

In some embodiments, the imparted colors of at least two externally visible surfaces of discrete elements will occupy a CIELab color space volume of less than about 200. The externally visible surfaces are analyzed according to the Test Method described below. Upon analysis, the inherent color of an element comprising an externally visible surface will yield L*, a*, and b* coordinates. The CIELab color space volume is then calculated using the formula presented above. The resulting volume can be less than about 200. The resulting volume can be less than about 50.

It should be recognized that the imparted colors of more than two discrete colored regions having a visible surface may occupy the aforementioned CIELab color space volumes. In calculating the CIELab color space volume for more than two elements, the CIELab color space volume is calculated using the maximum and minimum L*, a*, and b* from a set of elements. The maximum color values and minimum color values are used to calculate V according to the formula presented above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method of producing a multi-layered absorbent article, the method comprising the steps of:
   a. providing an absorbent article converting line;
   b. supplying a first precursor web to the converting line;
   c. printing a first composition to the first precursor web;
   d. supplying a second precursor web to the converting line;
   e. producing a composite substrate from the first and second precursor webs;
   f. supplying a lower substrate to the converting line;
   g. printing a second composition to the lower substrate;
   h. combining the composite substrate with the lower substrate to produce a laminate web; and
   i. cutting the laminate web into individual absorbent articles, wherein the method of printing the first composition and the second composition is via contact printing or non-contact printing, and wherein the method of printing the first composition is different than the method of printing the second composition.

2. The method of claim 1, wherein the first precursor web is a polymer film.

3. The method of claim 1, wherein the second precursor web comprises fibers.

4. The method of claim 3, wherein the second precursor web is an airlaid cellulosic mat.

5. The method of claim 1 further comprising the step of forming a tuft in the composite substrate.

6. The method of claim 5, wherein the first precursor web comprises a polymeric film, wherein the second precursor web comprises a nonwoven web, and wherein the first precursor web forms a cap over looped fibers of the second precursor web.

7. The method of claim 1, wherein the first composition forms a first colored region, and wherein the first composition is printed to a surface of the first precursor web that faces the lower substrate.

8. The method of claim 1, wherein the second composition forms a second colored region, and wherein the second composition is printed to a surface of the lower substrate that faces the composite substrate.

9. The method of claim 7, wherein the second composition forms a second colored region, and wherein the second composition is printed to a surface of the lower substrate that faces the composite substrate.

10. The method of claim 9, wherein the first colored region and the second colored region do not overlap with one another.

11. The method of claim 1, wherein the non-contact printing is done using an ink jet continuous binary array.

12. The method of claim 1, wherein the absorbent article is at least one of facial tissue, toilet tissue, paper towels, cleaning wipes, cleaning pads, sanitary napkins, pantiliners, tampons, interlabial devices, infant diapers, children's training pants, adult incontinence products, or absorbent wipes.

13. The method of claim 1, further comprising the step of bonding the laminate web.

14. The method of claim 2, wherein the polymeric film comprises apertures.

15. The method of claim 1, wherein the laminate web forms a portion of a feminine sanitary napkin, wherein the first precursor web forms a portion of a topsheet and wherein the lower substrate forms a portion of a secondary topsheet.

16. The method of claim 1 further comprising the step of severing the lower substrate into individual sheets and placing the individual sheets onto the composite web.

17. The method of claim 16 further comprising the step of providing an absorbent core web and cutting the absorbent core web into individual absorbent cores.

18. The method of claim 17 further comprising the step of placing the individual absorbent cores onto the individual sheets of lower substrate.

19. The method of claim 18 further comprising the step of placing a backsheet web over the individual absorbent cores to form a sandwich type web, bonding the sandwich type web, and cutting the sandwich type web.

\* \* \* \* \*